US011517393B2

(12) United States Patent
Hallack et al.

(10) Patent No.: US 11,517,393 B2
(45) Date of Patent: Dec. 6, 2022

(54) SYSTEMS AND METHODS FOR DETECTION AND ILLUMINATION OF REGIONS OF INTEREST

(71) Applicant: GENTEX CORPORATION, Zeeland, MI (US)

(72) Inventors: Jason D. Hallack, Allendale, MI (US); Joshua D. Lintz, Allendale, MI (US); David M. Falb, Grand Rapids, MI (US); Kurtis L. Geerlings, Zeeland, MI (US); William L. Tonar, Holland, MI (US); Bradley R. Hamlin, Allendale, MI (US); Jeremy A. Schut, Grand Rapids, MI (US); Mark A. VanVuuren, Dorr, MI (US); Steven J. Veenman, Hudsonville, MI (US); Jordan Miller, Rochester, MN (US); Heidi Nelson, Rochester, MN (US)

(73) Assignee: GENTEX CORPORATION, Zeeland, MI (US)

( * ) Notice: Subject to any disclaimer, the term of this patent is extended or adjusted under 35 U.S.C. 154(b) by 0 days.

(21) Appl. No.: 17/169,904

(22) Filed: Feb. 8, 2021

(65) Prior Publication Data
US 2021/0168919 A1    Jun. 3, 2021

Related U.S. Application Data

(63) Continuation of application No. 16/689,422, filed on Nov. 20, 2019, now Pat. No. 10,925,140, and a
(Continued)

(51) Int. Cl.
*H05B 47/10*    (2020.01)
*A61B 90/30*    (2016.01)
(Continued)

(52) U.S. Cl.
CPC .............. *A61B 90/30* (2016.02); *A61B 90/35* (2016.02); *A61L 2/084* (2013.01); *A61L 2/10* (2013.01);
(Continued)

(58) Field of Classification Search
CPC ...... H05B 47/10; H05B 47/11; H05B 47/125; H05B 47/165; A61B 90/30; A61B 90/35;
(Continued)

(56) References Cited

U.S. PATENT DOCUMENTS 10,517,158 B2 *  12/2019  Hallack ................... F21V 21/30
10,925,140 B2 *   2/2021  Hallack ................... H05B 47/10
(Continued)

FOREIGN PATENT DOCUMENTS

CN    204072839 U    1/2015
DE    102011007201 A1    5/2012
(Continued)

OTHER PUBLICATIONS

Extended European Search Report dated Mar. 24, 2021, for corresponding European application No. 19751259.3, 8 pages.
(Continued)

*Primary Examiner* — Haissa Philogene
(74) *Attorney, Agent, or Firm* — Price Heneveld LLP; Brian James Brewer

(57) ABSTRACT

An illumination system for a lighting assembly comprises a light assembly configured to selectively illuminate an operating region in a surgical suite and a plurality of light sources positioned within the light assembly and configured to emit light. The system further comprises at least one imager configured to capture image data and a controller. The controller is configured to scan the image data in at least one region of interest for a shaded region and identify a location of the shaded region within the region of interest. The
(Continued)

controller is further configured to control the light assembly to activate at least one of the light sources to emit light impinging on the shaded region within the region of interest.

19 Claims, 7 Drawing Sheets

Related U.S. Application Data continuation of application No. 16/271,007, filed on Feb. 8, 2019, now Pat. No. 10,517,158.

(60) Provisional application No. 62/628,760, filed on Feb. 9, 2018.

(51) Int. Cl.
| | | |
|---|---|---|
| *A61B 90/35* | (2016.01) | |
| *A61L 2/08* | (2006.01) | |
| *A61L 2/10* | (2006.01) | |
| *F21V 21/30* | (2006.01) | |
| *F21V 21/28* | (2006.01) | |
| *H04N 5/235* | (2006.01) | |
| *G06T 7/00* | (2017.01) | |
| *H05B 47/11* | (2020.01) | |
| *H05B 47/125* | (2020.01) | |
| *A61B 90/50* | (2016.01) | |
| *A61B 17/00* | (2006.01) | |
| *F21W 131/205* | (2006.01) | |
| *H05B 47/165* | (2020.01) | |

(52) U.S. Cl.
CPC ............. *F21V 21/28* (2013.01); *F21V 21/30* (2013.01); *G06T 7/00* (2013.01); *H04N 5/2354* (2013.01); *H05B 47/10* (2020.01); *H05B 47/11* (2020.01); *H05B 47/125* (2020.01); *A61B 2017/00203* (2013.01); *A61B 2017/00207* (2013.01); *A61B 2090/304* (2016.02); *A61B 2090/309* (2016.02); *A61B 2090/502* (2016.02); *A61L 2202/11* (2013.01); *A61L 2202/25* (2013.01); *F21W 2131/205* (2013.01); *H05B 47/165* (2020.01)

(58) Field of Classification Search
CPC .................. A61B 90/361; A61B 90/40; A61B 2017/00203; A61B 2017/00207; A61B 2090/309; A61B 2090/502; A61L 2/084; A61L 2/10; A61L 2202/14
See application file for complete search history.

(56) References Cited

U.S. PATENT DOCUMENTS

| | | | | |
|---|---|---|---|---|
| 2007/0121423 | A1* | 5/2007 | Rioux | G01V 1/16 367/69 |
| 2009/0225534 | A1* | 9/2009 | Thomas | F21V 21/084 362/105 |
| 2012/0330129 | A1* | 12/2012 | Awdeh | A61B 1/00048 600/411 |
| 2018/0020960 | A1* | 1/2018 | Sarussi | G01N 33/492 600/310 |
| 2019/0060026 | A1* | 2/2019 | Geerlings | A61B 90/361 |
| 2019/0249847 | A1* | 8/2019 | Hallack | F21V 23/0442 |
| 2020/0390392 | A1* | 12/2020 | Hallack | A61B 5/163 |

FOREIGN PATENT DOCUMENTS

| | | |
|---|---|---|
| JP | 2005518261 A | 6/2005 |
| JP | 2013502280 A | 1/2013 |
| JP | 2014220169 A | 11/2014 |
| JP | 2016515848 A | 6/2016 |
| JP | 2019513456 A | 5/2019 |
| WO | 2003072995 A1 | 9/2003 |
| WO | 2011022525 A1 | 2/2011 |
| WO | 2014139020 A1 | 9/2014 |
| WO | 2016197008 A1 | 12/2016 |
| WO | 2017148793 A1 | 9/2017 |
| WO | 2019043631 A1 | 3/2019 |

OTHER PUBLICATIONS

Japanese Office Action dated Jul. 1, 2021, for corresponding Japanese application No. 2020/543049, 6 pages.
English Translation of Japanese Office Action dated Jul. 1, 2021, for corresponding Japanese application No. 2020-543049, 6 pages.
Chinese First Office Action dated Mar. 25, 2022, for corresponding Chinese application No. 2019800204993, 7 pages.
Chinese Search Report dated Mar. 18, 2022, for corresponding Chinese application No. 2019800204993, 2 pages.

* cited by examiner

SYSTEMS AND METHODS FOR DETECTION AND ILLUMINATION OF REGIONS OF INTEREST

CROSS-REFERENCE TO RELATED APPLICATION

This application is a continuation of U.S. patent application Ser. No. 16/689,422, filed Nov. 20, 2019, entitled SYSTEMS AND METHODS FOR DETECTION AND ILLUMINATION OF REGIONS OF INTEREST, now U.S. Pat. No. 10,925,140, which is a continuation of U.S. patent application Ser. No. 16/271,007, filed Feb. 8, 2019, entitled SYSTEMS AND METHODS FOR DETECTION AND ILLUMINATION OF REGIONS OF INTEREST, now U.S. Pat. No. 10,517,158, which claims priority to and the benefit under 35 U.S.C. § 119(e) of U.S. Provisional Patent Application No. 62/628,760, filed on Feb. 9, 2018, entitled ADAPTIVE ILLUMINATION SYSTEMS WITH IMAGE-BASED CONTROL, the disclosures of which are hereby incorporated herein by reference in their entirety.

FIELD OF THE DISCLOSURE

The present disclosure generally relates to illumination systems and, more particularly, to surgical theater and surgical suite illumination systems.

BACKGROUND OF THE DISCLOSURE

Artificial lighting provided in surgical theaters and surgical suites may present a number of issues with regard to positioning, shadows, luminosity, and glare. Often, medical professionals are not stationary, and the lighting needs to be dynamic due to the shifting of personnel and instruments throughout the surgical procedure. Further, differences in the physical dimensions of personnel may make positioning light sources challenging. Accordingly, new illumination systems for surgical suites may be advantageous.

SUMMARY OF THE PRESENT DISCLOSURE

According to one aspect of this disclosure, an illumination system for a lighting assembly comprises a light assembly configured to selectively illuminate an operating region in a surgical suite and a plurality of light sources positioned within the light assembly and configured to emit light. The system further comprises at least one imager configured to capture image data and a controller. The controller is configured to scan the image data in at least one region of interest for a shaded region and identify a location of the shaded region within the region of interest. The controller is further configured to control the light assembly to activate at least one of the light sources to emit light impinging on the shaded region within the region of interest.

According to another aspect of this disclosure, a method for illuminating a region of interest in an operating region is disclosed. The method comprises capturing image data in a field of view representing the operating region and emitting a plurality of emission from a plurality of light sources. The method further comprises scanning the image data for at least one object position along an emission path between at least one of the light sources and a region of interest. Based on the detection of the object along the emission path, the method comprises identifying a location of the shaded region within the region of interest. The method further comprises controlling at least one of the plurality of light sources to emit light impinging on the shaded region within the region of interest.

According to yet another aspect of this disclosure, an illumination system for a surgical suite is disclosed. The illumination system comprises a light assembly configured to selectively illuminate an operating region in the surgical suite. A plurality of light sources is positioned within the light assembly and configured to emit light. At least one imager is configured to capture depth image data identifying a depth of at least one object in a field of view. The system further comprises a controller configured to scan the depth image data in at least one region of interest and generate a depth map of the operating region based on the depth image data and identify a position of at least one object located in the operating region based on the depth map. The controller is further configured to identify a location of a shaded region within the region of interest based on the position of the at least one object. Based on the location of the at least one object and the shaded region, the controller is configured to control the light assembly to activate at least one of the light sources to emit light impinging on the shaded region within the region of interest.

These and other aspects, objects, and features of the present disclosure will be understood and appreciated by those skilled in the art upon studying the following specification, claims, and appended drawings. It will also be understood that features of each example disclosed herein may be used in conjunction with, or as a replacement for, features of the other examples.

BRIEF DESCRIPTION OF THE DRAWINGS

The following is a description of the figures in the accompanying drawings. The figures are not necessarily to scale, and certain features and certain views of the figures may be shown exaggerated in scale or in schematic in the interest of clarity.

In the drawings.

DETAILED DESCRIPTION

Additional features and advantages of the invention will be set forth in the detailed description which follows and will be apparent to those skilled in the art from the description or recognized by practicing the invention as described in the following description together with the claims and appended drawings.

As used herein, the term "and/or," when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

In this document, relational terms, such as first and second, top and bottom, and the like, are used solely to distinguish one entity or action from another entity or action, without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

Figure 1:
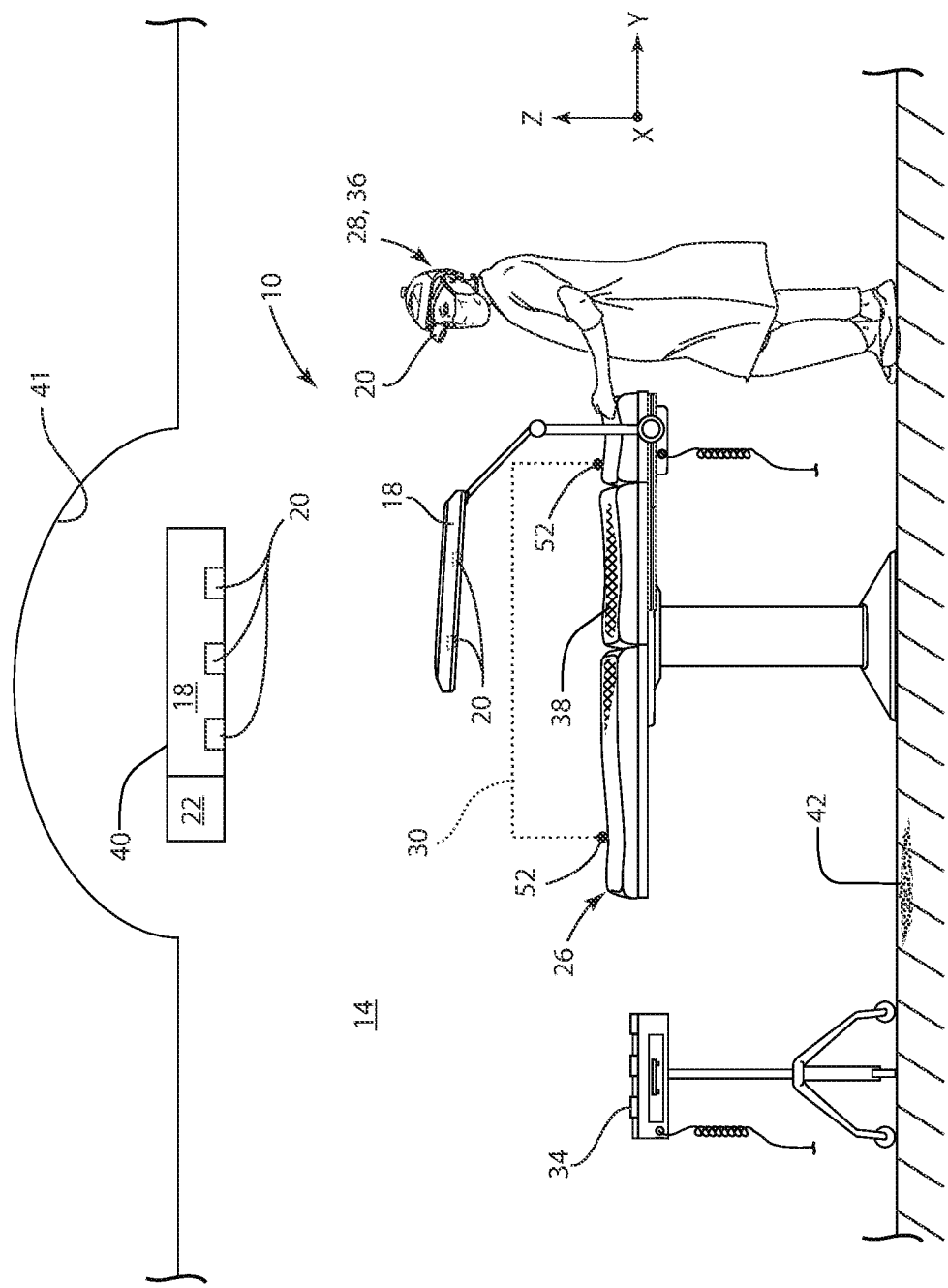
FIG. 1 is a schematic view of a surgical suite utilizing an illumination system.

Referring to FIG. 1, a schematic view of a surgical suite utilizing an illumination system 10 is shown. The illumination system 10 is depicted in a surgical suite 14 and includes one or more light assemblies 18. The light assemblies 18 may include one or more light sources 20. The illumination system 10 may include one or more imagers 22 depicted to aid in the use of the illumination system 10. The imager 22 may be positioned within or coupled to the light assemblies 18 (e.g., in handles or bodies), a table 26, a wearable device 28 and/or around the surgical suite 14. The imager 22 may be a charge-coupled device (CCD) imager, a complementary metal-oxide-semiconductor (CMOS) imager, other types of imagers and/or combinations thereof. According to various examples, the imager 22 may include one or more lenses to collimate and/or focus the light reflected by the patient, the table 26 or other features of the surgical suite 14.

The table 26 may at least partially define a surgical field 30. For purposes of this disclosure, the surgical field 30 may be an operating field, which may be an isolated area where surgery is performed. All furniture and equipment in the surgical field 30 may be covered with sterile drapes. Positioned within the surgical suite 14 may be one or more instruments 34 or tools that may be utilized in various procedures. Although described in connection with the surgical suite 14, it will be understood that the illumination system 10 of the present disclosure may be utilized in a variety of environments. For example, the illumination system 10 may be utilized in automobile repair areas, doctors' offices, dentistry, photography studios, manufacturing settings, as well as other areas where dynamic lighting solutions may be advantageous.

The table 26 may be configured to support a patient during a surgical procedure. According to various examples, the table 26 may have a square, rectangular and/or oval configuration. The table 26 may be composed of a metal (e.g., stainless steel), a polymer and/or combinations thereof. According to various examples, a sterile covering (e.g., a cloth or paper) may be positioned across a surface of the table 26. The table 26 may be configured to tilt, rotate and/or be raised or lowered. The tilting of the table 26 may be advantageous in allowing users (e.g., medical personnel) positioned around the table 26 to more easily access the patient and/or surgical field. In addition to tilting, it will be understood that the table 26 may be configured to raise or lower, rotate and/or slide about an X-Y plane.

As provided by various embodiments of the disclosure, the lighting system 10 may provide for adaptive lighting configured to detect lighting levels in the surgical suite 14. For example, the position of one or more instruments 34 and/or medical personnel 36 may cause one or more shadows 38 or shaded regions to form. The one or more imagers 22 of the system 10 may be configured to capture image data demonstrating the shadows 38. The image data may be supplied to a controller 40, which may identify the location of the shadows 38 in the surgical suite 14 and/or the surgical field 30. In response to identifying the shadows 38, the controller 40 may be configured to control the light assemblies 18 to alter the intensity, focus, and/or origin of the light emitted from the light assemblies 18 to illuminate the shadows 38. For example, the light control routine may auto adjust the intensity of one or more of the light sources 20 if another light source 20 gets blocked or begins producing shadows.

In some embodiments, the disclosure may further provide for the detection and/or treatment of potentially contaminated regions 42 of the surgical suite 14 and/or the surgical field 30. The contaminated regions 42 may correspond to regions where dirt, biological material, and/or bodily fluids (e.g. mucus, blood, saliva, urine, etc.) may be deposited in the surgical suite 14. Such material may be deposited as a result of one or more procedures or foreign contaminants shed by patients or personnel in the surgical suite 14. In such embodiments, the system 10 may be configured to selectively illuminate various regions in the surgical suite 14 with a detection emission of light ranging from approximately 25 nm to 600 nm. In response to receiving the detection emission, the contaminated regions 42 may absorb one or more bands of wavelengths in the detection emission. Based on the varying levels of absorption, the one or more imagers 22 may be configured to identify the contaminated regions 42.

In addition to identifying the contaminated regions 42, the system 10 may further provide for disinfection of the contaminated regions 42. For example, in some embodiments, one or more of the light sources 20 of the light assemblies 18 may be configured to emit wavelengths of germicidal light. Accordingly, in response to identifying the contaminated region 42 in the surgical suite 14, the controller 40 may activate a germicidal emission of the germicidal light to sterilize bacteria that may occupy the contaminated region 42. As discussed herein, the selective illumination of the region of the surgical suite 14 wherein the contaminated region 42 is located may be illuminated by selectively activating the light sources 20 and adjusting the intensity, focus, and/or origin from where the germicidal emission is emitted. The germicidal emission may comprise wavelengths of light ranging from approximately 260 nm to 270 nm. Such wavelengths may be emitted from one or more of the light sources 20, which may comprise Mercury-based lamps, Ultraviolet Light-Emitting Diode (UV-C LED) lamps, and/or pulsed-xenon lamps.

The light assemblies 18 may take a variety of configurations. The light assemblies 18 may include one or more light sources 20. In a first example, the light assemblies 18 may be modular and interconnected and supported by a track system. For example, the light assemblies 18 may have a circular, oval, oblong, triangular, square, rectangular, pentagonal or higher order polygon shape. It will be understood that different light assemblies 18 may take different shapes and that the illumination system may include a variety of light assemblies 18. The track system of the light assemblies 18 may allow for one or more light assemblies 18 to be moved relative to other light assemblies 18. The shape of the light assemblies 18 may be configured to allow the light assemblies 18 to "fit" or mate together along edges of the light assemblies 18. For example, square or triangular light assemblies 18 may be grouped in contact with one another or separated to form a larger shape (e.g., a cross, pentagon, freeform, etc.). According to various examples, the light assemblies 18 may be configured to snap together, or otherwise electrically and/or mechanically connect to one another. For example, the light assemblies 18 may share electrical power with one another once connected.

In various embodiments, the light assemblies 18 of the lighting system 10 may operate independently and may also operate in conjunction with one another. For example, each of the light assemblies 18 may comprise the controller 40 and/or be in communication with the controller 40. Accordingly, the controller 40 may selectively activate one or more of the light sources 20 of the light assemblies 18 providing for a scalable system to be formed by each of the light assemblies 18 controlled by the controller 40 in concert. In this way, the lighting system 10 may be scaled and flexibly implemented in various permanent or permanent installations in accordance with the disclosure.

In yet another example, the light assembly 18 may be configured to operate in conjunction with a mirror 41. The mirror 41 may be positioned above the table 26. In the depicted example, the mirror 41 is positioned in the ceiling of the surgical suite 14, but it will be understood that the mirror 41 may additionally, or alternatively, be suspended above the table 26. According to various examples, the mirror 41 may be concave such that light emitted by the light assembly 18 may be collimated and reflected toward the table 26 and/or the patient. In such an example, the light assembly 18 may include one or a plurality of light sources 20 positioned in a ring and configured to emit light toward the mirror 41. The light sources 20 may be positioned proximate a perimeter of the mirror 41 and/or proximate the table 26. Such an example of the light assembly 18 may be advantageous in allowing the light sources 20 and/or light assembly 18 to be positioned in unconventional locations away from a ceiling of the surgical suite 14.

As explained above, the light assemblies 18 may include one or more light sources 20 configured to emit visible and/or non-visible light. For example, the light sources 20 may be configured to emit visible light, infrared light (e.g., near-infrared and/or far-infrared) and/or ultraviolet light. In some examples, the light sources 20 may be strobed at a controlled frequency. Visible light examples of light from the light sources 20 may have a color temperature of from about 1,700 K to about 27,000 K. The color temperature of one or more of the light sources 20 may be variable across the color temperature range. In examples of the light sources 20 configured to emit infrared light, the infrared light may be used with one or more guidance systems (e.g., scanning and control systems) as described in greater detail below. In examples of the light sources 20 which emit ultraviolet light, the ultraviolet light alone, or in combination with other features (e.g., $TiO_2$ coatings, films and/or paints), may be configured to provide cleaning, sanitation and/or sterilization of surfaces (e.g., the table 26, instruments 34, the light assembly 18 and/or other portions of the surgical suite 14). For example, the ultraviolet light may be used in a photocatalytic process to kill bacteria, viruses, and/or to eliminate dirt and grime.

The light sources 20 may be light-emitting diodes, incandescent bulbs, and or other light-emitting sources. The light sources 20 may also be configured to emit light which excites a fluorescent dye. In such examples, the light may be referred to as an excitation emission. The excitation emission may be infrared, visible and/or ultraviolet light. In such examples, a fluorescent dye may be applied within the surgical site (e.g., incision or open cavity) of the patient such that application of the excitation emission to the patient causes the surgical site to fluoresce in visible light. Further, a biodegradable powder may be applied to the surgical site in the patient which may carry the fluorescent dye and/or be configured to reduce glare by scattering light off wet surfaces. In such an example, the biodegradable powder may be clear such that the underlying tissues are still visible, but alters the reflection of light such that the light is not specularly reflected and perceived as glare.

According to various examples, one or more of the light sources 20 is a light engine capable of producing unpolarized and/or polarized light of one-handedness including, but not limited to, certain liquid crystal displays (LCDs), laser diodes, light-emitting diodes (LEDs), incandescent light sources, halogen light sources and/or organic light-emitting diodes (OLEDs). In polarized light examples of the light sources 20, the light sources 20 are configured to emit a first-handedness polarization of light. According to various examples, the first-handedness polarization of light may have a circular polarization and/or an elliptical polarization. In electrodynamics, circular polarization of light is a polarization state in which, at each point, the electric field of the light wave has a constant magnitude, but its direction rotates with time at a steady rate in a plane perpendicular to the direction of the wave. A circularly polarized wave can be in one of two possible states, right-handedness circular polarization in which the electric field vector rotates in a right-hand sense with respect to the direction of propagation, and left-handedness circular polarization in which the vector rotates in a left-hand sense. Using the handedness convention, left- or right-handedness is determined by pointing one's left or right thumb toward the source, against the direction of propagation, and then matching the curling of one's fingers to the temporal rotation of the field. Elliptically polarized light may also be described as having a handedness in a substantially similar manner to that of the circularly polarized examples, but the electric vector varies in magnitude during rotation. Circular polarization of the light may be achieved when linearly polarized light from the light sources 20 passes through an integral or separate quarter-wave plate. Additionally, or alternatively, a reflective polarizer may be utilized. If a reflective polarizer is used on the light sources 20, as opposed to an absorbing polarizer, the light emitted by the light sources 20 that is the "wrong" polarization (e.g., the second-handedness polarization of light) is reflected back into the light source 20 where it can be "depolarized" and reflected back toward the polarizer.

In polarized examples of the light sources 20, as the surgical site of the patient is illuminated by the first-handedness polarization of light from the light sources 20, the moisture or water present within the patient may tend to specularly reflect the first-handedness polarization of light as the second-handedness polarization of light. As explained above, the first-handedness of polarization, once specularly reflected off of the patient may reverse in handedness to form the second-handedness polarization of light and be perceived by a human and/or machine (e.g., the imager 22) observer as glare. Generally, glare is the effect caused by the specular reflection of light reflected off of a smooth surface, such as a surface film of water. This glare can visually mask the details of the object below the reflecting surface and can obscure surrounding objects because the "glare" image appears brighter than surrounding objects. The reflected second-handedness polarization of light may be opposite from the first-handedness polarization of light. In examples where the first-handedness polarization of light is circularly polarized, the first and second polarizations of light are circularly polarized opposite from one another. In other words, the first and second polarizations of light may have an opposite handedness (e.g., left-handedness and right-handedness). As will be explained in greater detail below, an optical filter may be incorporated into the wearable device 28, into a filter positioned between the user and the patient, the imager 22 and/or into the movable screen example of the light assembly 18.

The light sources 20 may be light-emitting diodes, incandescent bulbs, and or other light-emitting sources. The light sources 20 may also be configured to emit light which excites a fluorescent dye. In such examples, the light may be referred to as an excitation-emission. The excitation-emission may be infrared, visible and/or ultraviolet light. In such examples, a fluorescent dye may be applied within the surgical site (e.g., incision or open cavity) of the patient such that application of the excitation-emission to the patient causes the surgical site to fluoresce in visible light. Further, a biodegradable powder may be applied to the surgical site in the patient which may carry the fluorescent dye and/or be configured to reduce glare by scattering light off wet surfaces. In such an example, the biodegradable powder may be clear such that the underlying tissues are still visible, but alters the reflection of light such that the light is not specularly reflected and perceived as glare.

Figure 2:
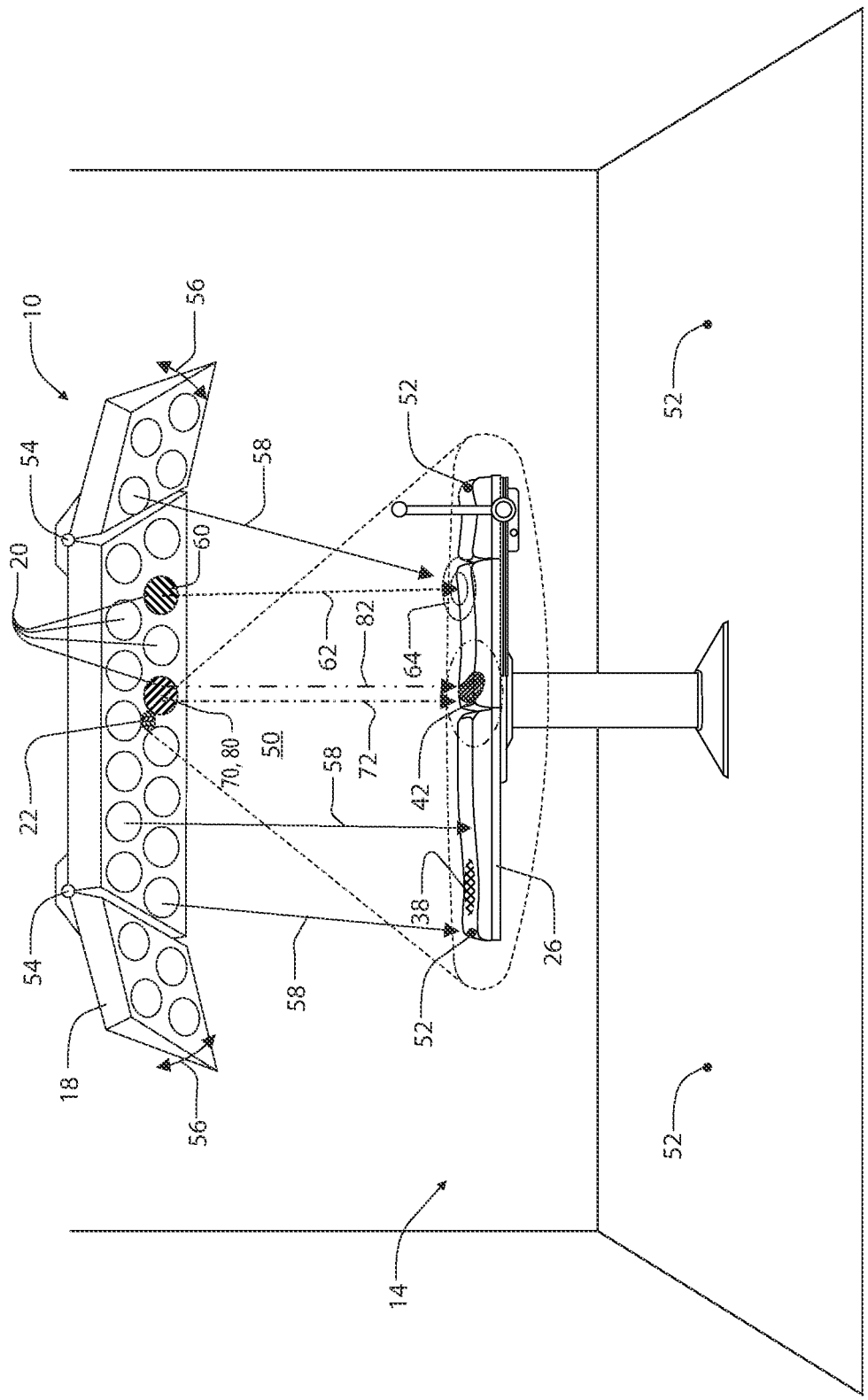
FIG. 2 is a schematic view of a surgical suite comprising an illumination system configured for adaptive lighting.

FIG. 2 demonstrates a schematic view of a surgical suite comprising an illumination system configured for adaptive lighting. Referring now to FIGS. 1 and 2, the illumination system 10 may include one or more imagers 22. The imager 22 may be configured to capture image data in a field of view 50 capturing at least a portion of the surgical suite 14 and/or from the surgical field 30. The imager 22 may be configured to relay visual information to the controller 40 of the illumination system 10. The controller may include a memory and a processor. The memory may store computer executable commands (e.g., routines) which are controlled by the processor. According to various examples, the memory may include a light control routine and/or an image analyzing routine. The image analyzing routine is configured to process data from the imager 22. For example, the image analyzing routine may be configured to identify shadows and luminosity of the surgical filed 30, the light from the guidance system, location of points of interest (e.g., users around the table 26, the wearable device 28) and/or gestures from the users. The controller 40 is further discussed in reference to FIG. 7, which illustrates an exemplary block diagram of the system 10.

According to various examples, the image analyzing routine may also be configured to identify the location of a plurality of markers 52 within the image. The markers 52 may be symbols, computer readable codes and/or patterns which designate a point of interest in the image. For example, a plurality of markers 52 can be positioned around the surgical field 30 such that the image analyzing routine may determine the perimeter of the surgical field 30. Further, one or more markers 52 may be positioned on the instruments 34, the users, points of interest in the surgical suite 14 and/or the patient. The image analyzing software may or may not track light from the guidance system outside of the perimeter indicated by the markers 52 and/or the surgical field 30.

Once the image analyzing routine has processed the data from the imager 22, the light control routine may control how the light assemblies 18 are operated. For example, the light control routine may be configured to move, steer, activate or otherwise influence the light assemblies 18 to emit light where the user is looking or working (e.g., as measured from the guidance system). In such embodiments, the system 10 may comprise one or more positioning devices 54 (e.g., a motor, actuator, etc.), which may correspond to electro-mechanical systems configured to adjust a position and or projection direction 56 of one or more of the light sources 20. In static, or fixed, examples of the light sources 20, the light sources 20 may be assigned to focus on various predefined points (e.g., on a patient and/or on the table 26).

In some embodiments, the controller 40 may process and control the system 10 to complete a light control routine. The light control routine may selectively activate and\or steer lighting emissions 58 from the light sources 20 adjusting an orientation, position, and/or a location of origin of the lighting emissions 58 based on the shadows 38 or variations in illumination in the surgical suite 14. The light control routine may gradually adjust the position or orientation of the lighting emissions 58 to minimize uncomfortable fast switching of illumination. In this way, the system 10 may provide for the detection and selective illumination of various portions of the surgical suite 14.

It will be understood that any and all features described in connection with the light sources 20 may be applied to any and all of the examples of the light assemblies 18. For example, the in situ light assembly 18 may include pixelated and/or independently movable light sources 20 while the movable light assembly 18 may emit polarized light. Further, the steerable examples of the light sources 20 may be applied to any of the light assembly 18 examples.

According to various examples, one or more users positioned within the surgical suite 14 may include the wearable device 28. The wearable device 28 may be eyewear (e.g., goggles, eye glasses), headwear (e.g., a face shield, helmet, visor, etc.), a garment and/or combinations thereof. In eyewear examples, the wearable device 28 may be configured to enhance (e.g., by increased transmission) or eliminate one or more wavelengths or wavelength bands of light. For example, when using the fluorescent dye explained above, the wearable device 28 may allow all light of the wavelength emitted from the fluorescent dye to pass through the wearable device 28. Such a feature may be advantageous in allowing a greater visibility of the fluorescent dye which may result in a higher perceived luminance of the surgical site.

In another example, the wearable device 28 may be configured to eliminate one or more polarizations of light. As explained above, specularly reflected circularly polarized light may reverse in handedness. The wearable device 28 may be configured to allow the first-handed polarization of light to pass, while eliminating the second-handedness polarization of light to minimize glare. According to various examples, polarization filtering may be accomplished by an optical filter within the wearable device 28. The optical filter is configured to reflect and/or absorb the second-handedness polarization of light. The optical filter may include one or more reflective polarizers and/or absorptive polarizers. In such examples, the optical filter may be referred to as a polarizer. Reflective polarizer examples may include a wire grid polarizer plus a quarter wave plate or optical retarder, a multilayer plastic film, such as a dual brightness enhancement film (DBEF) polarizer with a quarter wave plate, an optical retarder and/or a liquid crystal material. DBEF film or absorbing polarizer examples of the optical film may have a transmittance of ambient light and/or the first-handedness polarization of light incident on the optical filter of about 5%, 10%, 20%, 30%, 40%, 45%, 49%, 50%, 60%, 70%, 80%, 90% or greater than about 99%. Further, the optical filter may have a reflectance and/or absorbance of about 5%, 10%, 20%, 30%, 40%, 45%, 49%, 50%, 60%, 70%, 80%, 99% or greater of the second-handedness polarization of light. Removal of the second-handedness polarization of light may reduce and/or eliminate a perceived glare off of the surgical site. The color of the first-handedness polarization of light which passed through the optical filter may be a fairly neutral gray to avoid influencing the natural visible colors.

According to various examples, the wearable device 28 may be shuttered and linked to one or more of the light assemblies 18 and the illumination system 10 to provide different lighting for different users. For example, in strobed examples of the light sources 20, different wearable devices 28 may provide different shutter speeds and delays such that a perceived intensity of the light is different for different users. Such a feature may be programmed into the wearable device 28 or may be adjusted dynamically during surgery.

According to various examples, the wearable device 28 may be configured to reflect and/or to emit light. In reflective examples, the wearable device 28 may include a mirror 41 or other reflective surface configured to collect, reflect, redirect and/or collimate light from one or more of the light assemblies 18. For example, the reflective element of the wearable device 28 may include one or more galvanometers and/or gyroscopes which change the reflection axis of the reflective element to redirect the light from the light assembly 18 to where the wearer is looking. Additionally, or alternatively, the wearable device 28 may include one or more light sources 20. Efficiency of the light sources 20 may be increased by turning the light sources 20 on and off based on whether the wearer is looking at the surgical field 30, only turning on light sources 20 that are pointed at the field 30 (e.g., while shutting off light sources 20 that are pointing away) and/or by adjusting the intensity of light based on measured lighting and/or shadowing of the area the user is looking at. According to various examples, the wearable device 28 may be lighter and/or have an increased battery time compared to conventional lighting systems. Further, the wearable device 28 may be cordless. Further, the wearable device 28, in eyewear examples, may provide magnification of light.

According to various examples, the wearable device 28 may include one or more guidance systems. The guidance systems may include a feature to indicate where the wearer is looking and/or working. For example, the guidance system may include a laser emitting visible and/or nonvisible (e.g., infrared) light. The light emitted from the guidance system may be tracked by the imager 22 and relayed to the illumination system 10. Such tracking of the light emitted from the guidance system may allow the illumination system 10 to emit light from the light assemblies 18 where the user is looking.

As explained above, the illumination system 10 may include one or more imagers 22 which capture image data from the surgical suite 14 and/or from the surgical field 30. The imager 22 may be configured to relay visual information to a controller of the illumination system 10. The controller 40 may include a memory and a processor. The memory may store computer executable commands (e.g., routines) which are controlled by the processor. According to various examples, the memory may include a light control routine and/or an image analyzing routine. The image analyzing routine is configured to process data from the imager 22. For example, the image analyzing routine may be configured to identify shadows and luminosity of the surgical field 30, the light from the guidance system, location of points of interest (e.g., users around the table 26, the wearable device 28) and/or gestures from the users. According to various examples, the image analyzing routine may also be configured to identify the location of a plurality of markers 52 within the image. The markers 52 may be symbols, computer readable codes and/or patterns which designate a point of interest in the image. For example, a plurality of markers 52 can be positioned around the surgical field 30 such that the image analyzing routine may determine the perimeter of the surgical field 30. Further, one or more markers 52 may be positioned on the instruments 34, the users, points of interest in the surgical suite 14 and/or the patient. The image analyzing software may or may not track light from the guidance system outside of the perimeter indicated by the markers 52 and/or the surgical field 30.

Once the image analyzing routine has processed the data from the imager 22, the light control routine may control how the light assemblies 18 are operated. For example, the light control routine may be configured to move, steer, activate or otherwise influence the light assemblies 18 to emit light where the user is looking or working (e.g., as measured from the guidance system). In a first example, the light control routine may steer or otherwise move the emitted light from the light sources 20 to track where the user is looking and/or where hands and instruments 34 are positioned. The light control routine may slow the speed of movement of the light relative to the movement of the user's gaze to minimize uncomfortable fast switching of illumination. In a second example, when the user's gaze is detected outside of the surgical field 30, the light assemblies 18 may be configured to emit light toward a last known gaze position. Further, the light control routine may be configured to switch off one or more light sources 20 positioned on the wearable device 28 to conserve its power. Third, the light control routine may control one or more of the lighting assemblies 18 based on gesture control. For example, where the light from different lighting assemblies 18 is directed may be indicated by gestures (e.g., displaying a single finger at a point where a first light source 20 should shine and displaying two fingers at a location where a second light source 20 should shine). Other exemplary gestures which the light control routine may respond to may include pinching to enlarge or contract the light beam. Steering of the light from the light sources 20 may be accomplished by any of the methods outlined above. In a third example, the light control routine may respond to the location and orientation of markers positioned on the user (e.g., on a head or hands/gloves).

For example, illumination from the light assemblies 18 may be moved or altered based on the head and/or hand orientation of the user. Further, the light control routine may be configured to direct or steer light from one or more of the light sources 20 to the reflector of the wearable device 28. For example by monitoring the user and movement of the marker, the image analyzing routine may determine where the reflector is and emit light at the appropriate angle towards it to illuminate the surgical site. In a fourth example, one or more of the imagers 22 may be a visible light camera which can detect shadowing and the light control routine may alter the illumination accordingly. For example, the light control routine may auto adjust the intensity of one or more of the light sources 20 if another light source 20 gets blocked or begins producing shadows. It will be understood that the light control routine may also be controlled via voice or mechanical input (e.g., foot) without departing from the teachings provided herein. In a fifth example, the light control routine may be configured to turn off one or more lights automatically. For example, if the light control routine detects that a light source 20 will shine in a user's eyes or produce glare due to the angle of the light and positioning of a user, the light control routine will automatically turn off the offending light source and compensate by activating other light sources 20 and/or increasing the luminance of the other light sources.

Still referring to FIG. 2, in some embodiments, the imager 22 may be used in conjunction with one or more infrared emitters 60. Though demonstrated as a single infrared emitter in FIG. 2, the system 10 may comprise a plurality of infrared emitters 60 distributed throughout the light assemblies 18. In operation, the infrared emitters 60 may project an infrared emission 62 comprising a field of infrared dots 64 into the surgical suite 14. The infrared dots 64 may be detected by one or more image processors of the controller 40 based on the image data captured by the imager 22 demonstrating the field of view 50. In response to the detection, the controller 40 may identify the relative position of the infrared dots 64 and control one or more of the light sources 20 and the positioning devices 54 to direct lighting emissions 58 to illuminate a desired location in the surgical suite 14.

The controller 40 may identify a location of the infrared dots 64 in the surgical suite 14 by applying one or more image analyzing routines and a three-dimensional map of the surgical suite 14. With the three-dimensional map, any of the above-noted light control routine operations may be performed. Additionally, in order to direct the lighting emissions 58 (or various electromagnetic emissions discussed herein), the position of each of the light sources 20 and any range of motion of the projection direction 56 may be calibrated to the controller 40. Accordingly, once the location of a shadow 38 or any point of interest is identified by the controller 40 based on the infrared dots 64, the controller 40 may selectively direct one or more of the lighting emissions 58 to illuminate the shadow 38. In this way, the controller 40 may control the activation, orientation, and/or origin of the light sources 20 to illuminate a desired region or portion of the surgical suite 14.

The controller 40 may also be configured to identify a location of the shadow 38 or various other points of interest (e.g., the contaminated region 42) or any various portions or regions of the surgical suite by applying one or more image recognition techniques. For example, the illumination system 10 may be configured to track the location and use of the instruments 34. For example, the instruments 34 may include a paint, marker and/or indicator which can be seen (e.g., infrared reflective and/or fluorescent) by the imager 22. Additionally, the controller 40 may be configured to detect one or more portions of the personnel 36, the table 26, a patient, or various shapes or characters captured in the image data in the field of view 50. The instruments 34 may be coded based on type (e.g., consumable tool vs. non-consumable) and/or by the operator using or placing them. The instruments 34 may be tracked as they enter and exit the surgical field 30 by showing them to imager 22. In some examples, one or more of the instruments 34 may include a radio frequency identification tracking device, which may be identified by the controller 40 for presence detection and located based on triangulation or other methods.

Still referring to FIG. 2, the system 10 may further be configured to detect and/or sterilize potentially contaminated regions 42 of the surgical suite 14 and/or the surgical field 30. The contaminated regions 42 may correspond to regions where dirt, biological material, and/or bodily fluids (e.g., mucus, blood, saliva, urine, etc.) may be deposited in the surgical suite 14. Such material may be deposited as a result of one or more procedures or foreign contaminants shed by patients or personnel in the surgical suite 14. In such embodiments, the system 10 may comprise one or more detection emitters 70 configured to selectively illuminate various regions in the surgical suite 14 with a detection emission 72. The detection emission 72 may consist of light ranging from approximately 25 nm to 600 nm. In response to receiving the detection emission, the contaminated regions 42 may absorb one or more bands of wavelengths in the detection emission 72. Based on the varying levels of absorption, the one or more imagers 22 may be configured to identify the contaminated regions 42. The imager 22 may comprise one or more color filters or colored lenses (e.g. a yellow or orange lens) that may emphasize or improve the detection contaminated regions 42.

In addition to identifying the contaminated regions 42, the system 10 may further provide for disinfection of the contaminated regions 42. For example, in some embodiments, the light sources 20 of the light assemblies 18 may comprise one or more sterilization emitters 80 configured to sterilization emissions 82 comprising wavelengths of germicidal light. Accordingly, in response to identifying the contaminated region 42 in the surgical suite 14, the controller 40 may activate the sterilization emission 82 of germicidal light such that the emission 82 impinges up the contaminated region 42 for sterilization. The sterilization emission 82 may comprise wavelengths of light ranging from approximately 250 nm to 290 nm. Such wavelengths may be emitted from one or more of the light sources 20, which may comprise Mercury-based lamps, Ultraviolet Light-Emitting Diodes (UV-C LED) lamps, and/or pulsed-xenon lamps.

Figure 3:
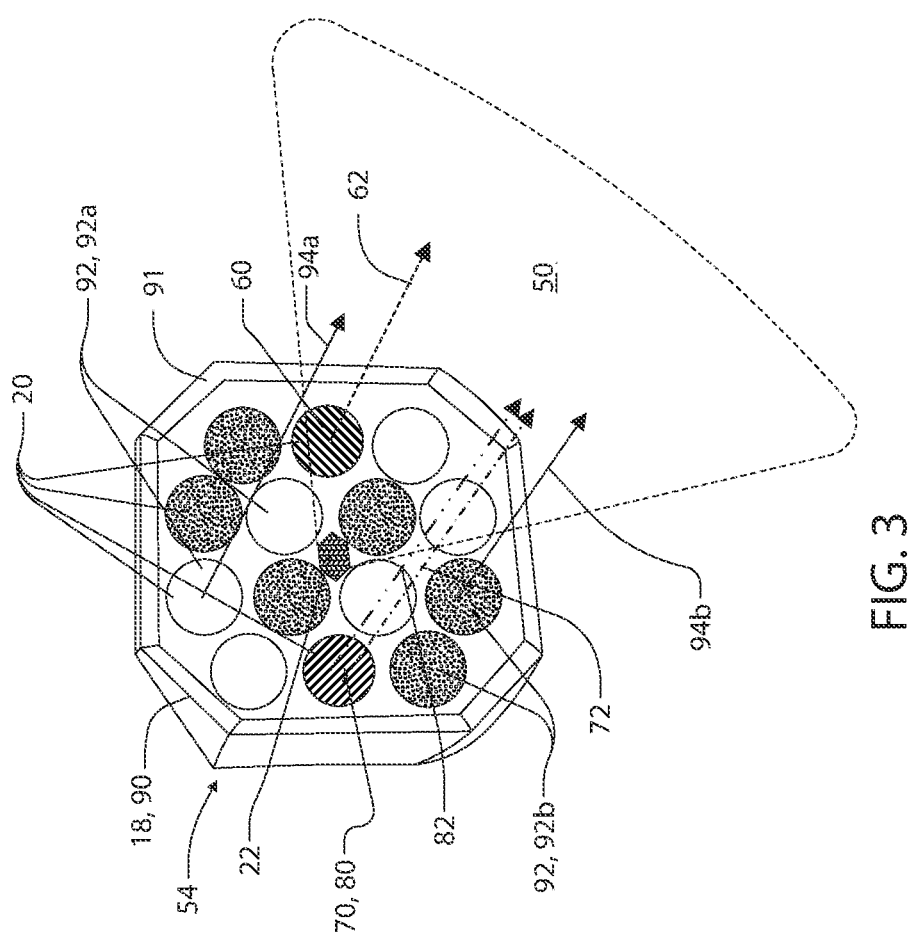
FIG. 3 is a schematic view lighting module of an illumination system.

Referring to FIG. 3, a schematic view lighting module of an exemplary embodiment of the lighting assemblies 18 is demonstrated and will be referred to as a lighting module 90. The lighting module 90 may comprise the plurality of light sources 20 disposed in a housing 91 or enclosure. The housing 91 may be configured to house the light sources 20, the one or more imagers 22, and may be configured to be suspended or otherwise mounted to one or more of the positioning devices 54. In this configuration, the lighting module 90 may provide for a modular assembly that may be utilized in a variety of applications.

The light sources of the lighting module 90 may comprise a plurality of visible light sources 92. The visible light sources 92 may comprise two or more different light sources configured to emit different color temperatures of light. For example, a first visible light source 92*a* may be configured to emit a warm light emission 94*a* (e.g. approximately 4000K color temperature). Additionally, a second visible light source 92*b* may be configured to emit a cool light emission 94*b* (e.g., approximately 6500K color temperature). Each of the emissions 94*a* and 94*b* may not be limited to the specific color temperatures discussed herein. Accordingly, the terms warm and cool may refer to the relative color temperature of the emissions 94*a* and 94*b* in the exemplary embodiment. Accordingly, the controller 40 may selectively activate each of the light sources 92*a* and 92*b* to emit the emission 94*a* and 94*b*. In this way, the system 10 may provide for a lighting module 90 operable to control a desired lighting intensity, light beam extent or scope, and color temperature to provide dynamic lighting.

The light sources 20 may further comprise one or more of the infrared emitters 60, the detection emitters 70, and/or the sterilization emitters 80. As previously discussed, the infrared emitters 60 may project an infrared emission 62 comprising a field of infrared dots 64 into the surgical suite 14. The detection emitters 70 may be configured to emit a detection emission 72 into the surgical suite 14 to selectively illuminate one or more contaminated regions 42 for sterilization. The sterilization emitters 80 are configured to emit the sterilization emissions 82 to sterilize the surgical suite 14 including one or more specific locations identified by the controller 40 where the contaminated regions 42 are identified. Accordingly, in various embodiments, the disclosure provides for a multi-purpose, intelligent adaptive lighting system that may be implemented in the surgical suite 14 or a variety of similar applications.

Figure 4:
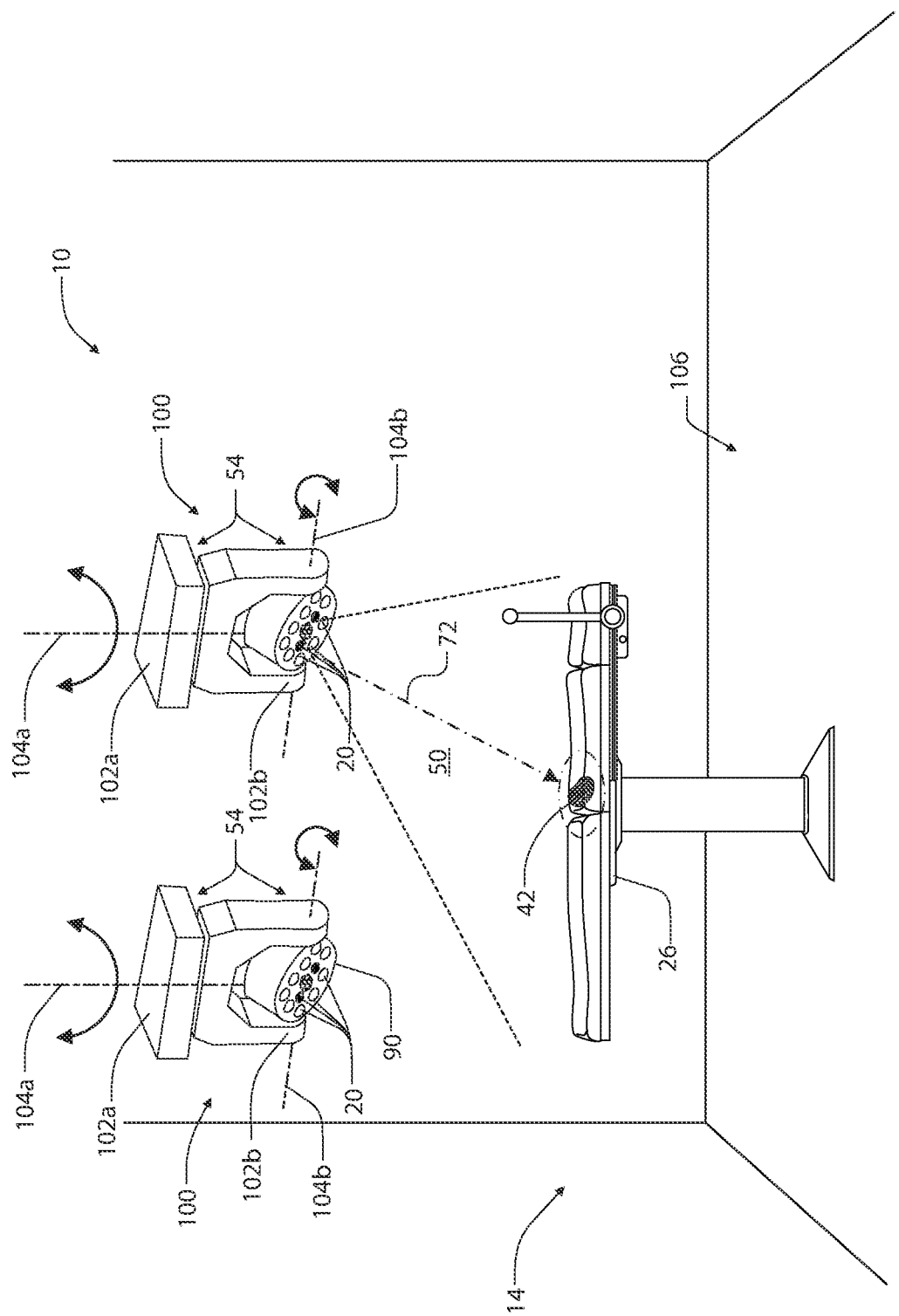
FIG. 4 is a schematic view of a surgical suite comprising an illumination system comprising an articulating head assembly configured for adaptive lighting.

FIG. 4 is a schematic view of the surgical suite 14 comprising the illumination system 10 incorporating an articulating head assembly 100. Referring to FIGS. 3 and 4, the articulating head assembly 100 may serve as an exemplary embodiment of the one or more positioning devices 54 in accordance with the disclosure. As illustrated in FIG. 4, a plurality of the lighting modules 90 are shown suspended from a ceiling of the surgical suite 14 by the head assemblies 100. The head assemblies 100 may be in connection with the housing 91 of the lighting module 90. The head assembly 100 may comprise a first actuator 102a configured to rotate the lighting module 90 about a first axis 104a (e.g. the Y-axis). The head assembly 100 may further comprise a second actuator 102b configured to rotate the lighting module 90 about a second axis 104b (e.g. the X-axis). In this configuration, the lighting module 90 may be suspended above the table 26 in the surgical suite 14 and the controller may be configured to control the actuators 102a and 102b to aim or direct each of the emissions (e.g., 60, 70, 80, 94a, and/or 94b) as well as the field of view 50 of the imager 22 throughout the surgical suite.

The head assembly 100 may comprise one or more gimbaled arms, which can be maneuvered or adjusted in response to a movement (e.g., rotational actuation) of the actuators 102a and 102b. In this configuration, the controller 40 may be configured to control each of the actuators 102a and 102b to manipulate the orientation of the lighting module 90 on the head assembly 100 by controlling the rotation of the lighting module 90 about the first axis 104a and the second axis 104b. Such manipulation of the lighting module 90 may enable the controller 40 to direct the light sources 20 and the imager 22 to illuminate, sterilize, and/or detect an entire floor surface 106 of the surgical suite 14. In this way, the system 10 may provide an increased range of motion and increased operating region for the one or more of the light assemblies 18 as discussed herein.

Though the imager 22 is shown incorporated in each of the lighting modules 90, the imager 22 may be located remotely from the lighting module 90. For example, a single imager 22 may be centrally located in the surgical suite 14 in connection with a central controller. The central controller may be configured to process the image data captured by the imager 22 and control each of the head assemblies by communicating control signals to each of the controllers 40. In this way, each of the lighting modules 90 may not be required to include an imager 22 and may also not be required to independently process the image data. However, in some embodiments, incorporating the imagers 22 in each of the lighting modules 90 may be beneficial to provide additional fields of view.

The positioning devices 54 and actuators 102a, 102b, as discussed herein, may correspond to one or more electrical motors (e.g., servo motors, stepper motors, etc.). Accordingly, each of the positioning devices 54 (e.g. the actuators 102) may be configured to rotate the lighting module 360 degrees or within the boundary constraints of head assembly 100 or other support structures that may support the light assemblies 18. The controller 40 may control the one or more positioning devices 54 (e.g. motors) to direct each of the emissions (e.g., 60, 70, 80, 94a, and/or 94b) of the light sources 20 as well as the field of view 50 of the imager 22 to target a desired location in the surgical suite 14. In order to accurately direct the lighting module 90 to target the desired location, the controller 40 may be calibrated to control the position of the lighting module 90 to target locations in a grid or work envelope of the surgical suite 14. The calibration of such a system may require maintenance in the form of calibration updates or compensation due to variations in operation of the positioning devices 54 and actuators 102 that may occur over time.

In some embodiments, the light assemblies 18 may also be positioned on a track assembly. In such embodiments, the light assemblies 18 may also be configured to translate along the first axis 104a and the second axis 104b. Such a configuration of the lighting system 10 may provide a greater range of movement such that the controller 40 can reach regions of the surgical suite 14 that may be occluded or otherwise unreachable by the emissions (e.g., 60, 70, 80, 94a, and/or 94b) of the light sources 20 as well as the field of view 50 of the imager 22.

Figure 5:
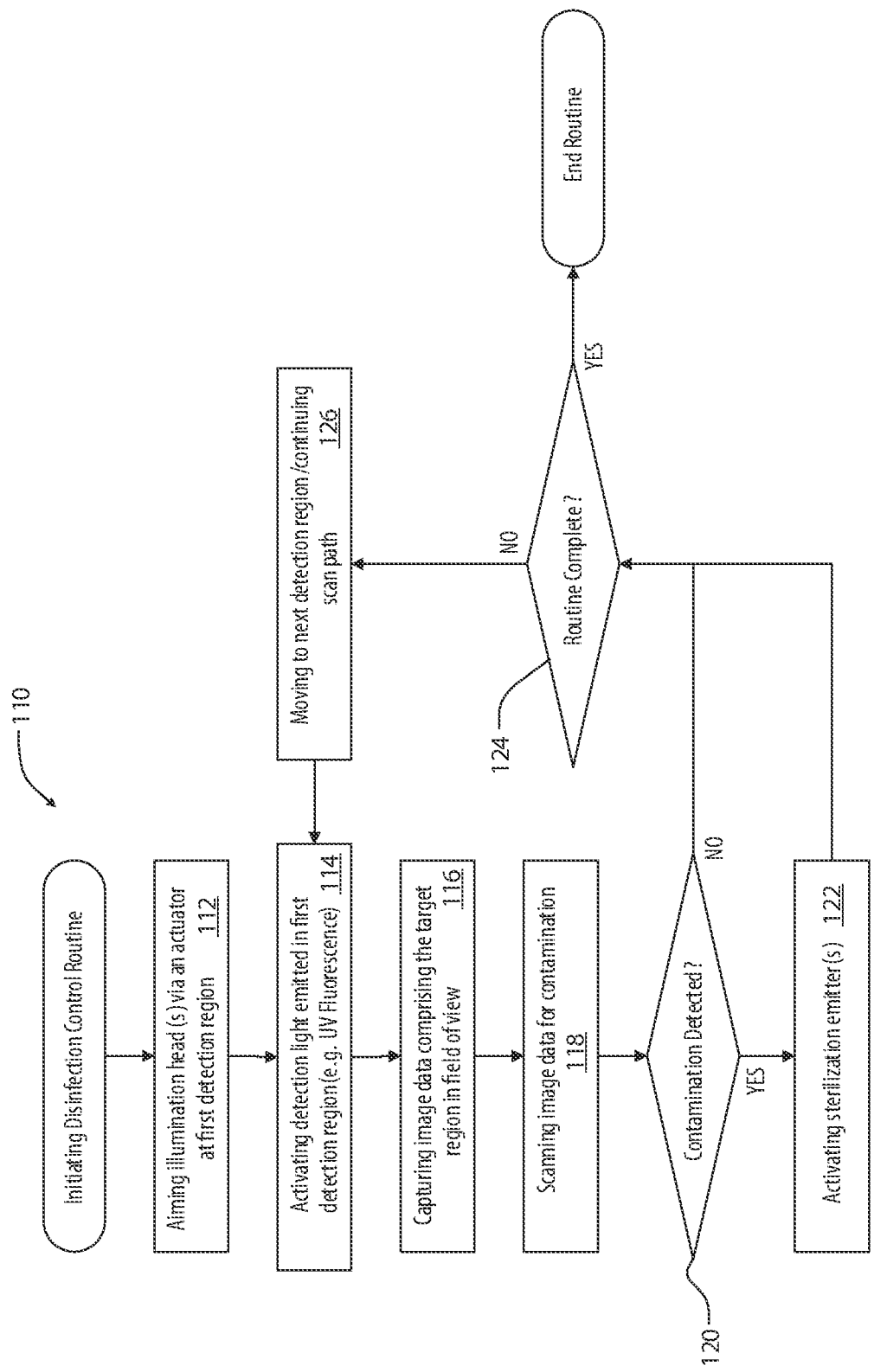
FIG. 5 is a flowchart demonstrating a disinfection routine for adaptive lighting.

Referring to FIG. 5, a flowchart is shown demonstrating a disinfection routine 110 for the system 10 configured to provide adaptive lighting. The routine 110 may begin by aiming the lighting module 90 with the head assembly 100 (112). In general, the disinfection routine 110 may comprise treating one or more regions of the surgical suite with one or more emissions of the sterilization emission 82. In some embodiments, the sterilization emissions 82 may be emitted from each of a plurality of the lighting modules 90. For example, a central controller may control each of the controllers 40 or each of the controllers 40 may be configured to communicate and operate in coordination to direct the sterilization emission 82 to one or more regions in the surgical suite. In this way, the intensity of the sterilization emission 82 delivered to a target region may be significantly increased. In doing so, the system 10 may be operable to reduce a sterilization time for one or more regions in the surgical suite 14.

In some embodiments, the system 10 may be configured to control the controllers 40 to direct one or more of the sterilization emissions 82 to systematically sweep the surgical suite 14. Such operation may be completed by sweeping over the entirety of the surgical suite along a fixed, sweeping path or raster path until the sterilization emission 82 have been delivered to the reachable or unobstructed surfaces for a prescribed time necessary for sterilization. In some embodiments, one of more regions of the surgical suite may be prioritized for sterilization. For example, the table 26 and other regions in the surgical suite may be identified as primary treatment regions. Accordingly, the system 10 may control one or a plurality of the lighting modules 90 to direct the sterilization emissions 82 to sweep the table 26 prior to completing a full sweep of various remaining or secondary portions of the surgical suite 14.

In embodiments implementing the plurality of lighting modules 90 and/or emitters 80 distributed in different regions of the surgical suite 14, the controllers 40 or a central controller may control the emitter to treat regions closer in proximity or localized to each of the emitters 80. For example, in an embodiment comprising four lighting modules 90 and head assemblies 100 configured to adjust the projection direction of the emitters 80 independently. Each of the head assemblies 100 and the corresponding actuators 102 may be controlled by the controllers 40 or a central controller in communication with the controllers to complete localized sterilization treatment sweeps by applying raster treatment paths in separate quadrants of the surgical suite 14. Each of the quadrants treated by the lighting modules 90 may correspond to a region or quadrant nearest each of the four respective lighting modules 90 and corresponding sterilization emitters 80. In this way, the system 10 may prioritize one or more regions for sterilization and/or complete a systematic treatment of the surgical suite 14 with the sterilization emissions 82.

Referring again to FIG. 5, the controllers 40 or a central controller may additionally be operable to detect one or more of the contaminated regions 42 for treatment. The system 10 may detect the contaminated regions 42 by maneuvering the head assemblies 100 to scan the surgical suite 14. In order to maneuver the head assemblies 100, the controllers 40 or a central controller may control the positioning devices 54 (e.g., the actuators 102) to aim the emissions (e.g., 60, 70, 80, 94*a*, and/or 94*b*) of the light sources 20 as well as the field of view 50 of the imager 22 to initial detection regions. The detection regions and corresponding paths of the lighting modules 90 may be different or distinct covering non-overlapping portions of the surgical suite 14. For clarity, the routine 110 is discussed in reference to a single lighting module 90 in reference to FIG. 5. Once the lighting module 90 is aimed at the initial detection region, the controller may activate the detection emitter 70 in the first detection region (114). While the detection emitter 70 is emitting the detection emission 72, the controller 40 may capture and process image data in the field of view 50 directed at the first target region (116). The controller 40 may then process the image data to identify the contaminated regions 42 (118).

Based on the image data, the controller 40 may determine if the contamination region is detected (120). If the contaminated region 42 is identified in the image data, the controller 40 may activate the sterilization emitters 80 (122). The controller 40 may maintain the activation of the sterilization emitters to direct the sterilization emission 82 at the contaminated region 42 for a predetermined time. If the contaminated region 42 is not identified in the image data, the controller 40 may continue to step 124 to determine if the routine 110 is complete. If the routine 110 is not complete, the controller 40 may continue to control the positioning device 54 (e.g., the actuators 102) to aim the emissions (e.g., 60, 70, 80, 94*a*, and/or 94*b*) of the light sources 20 as well as the field of view 50 of the imager 22 to a second target region (126). If the routine 110 is complete in step 124, the controller 40 may end the routine and continue to position the head assembly in a home position.

Figure 6:
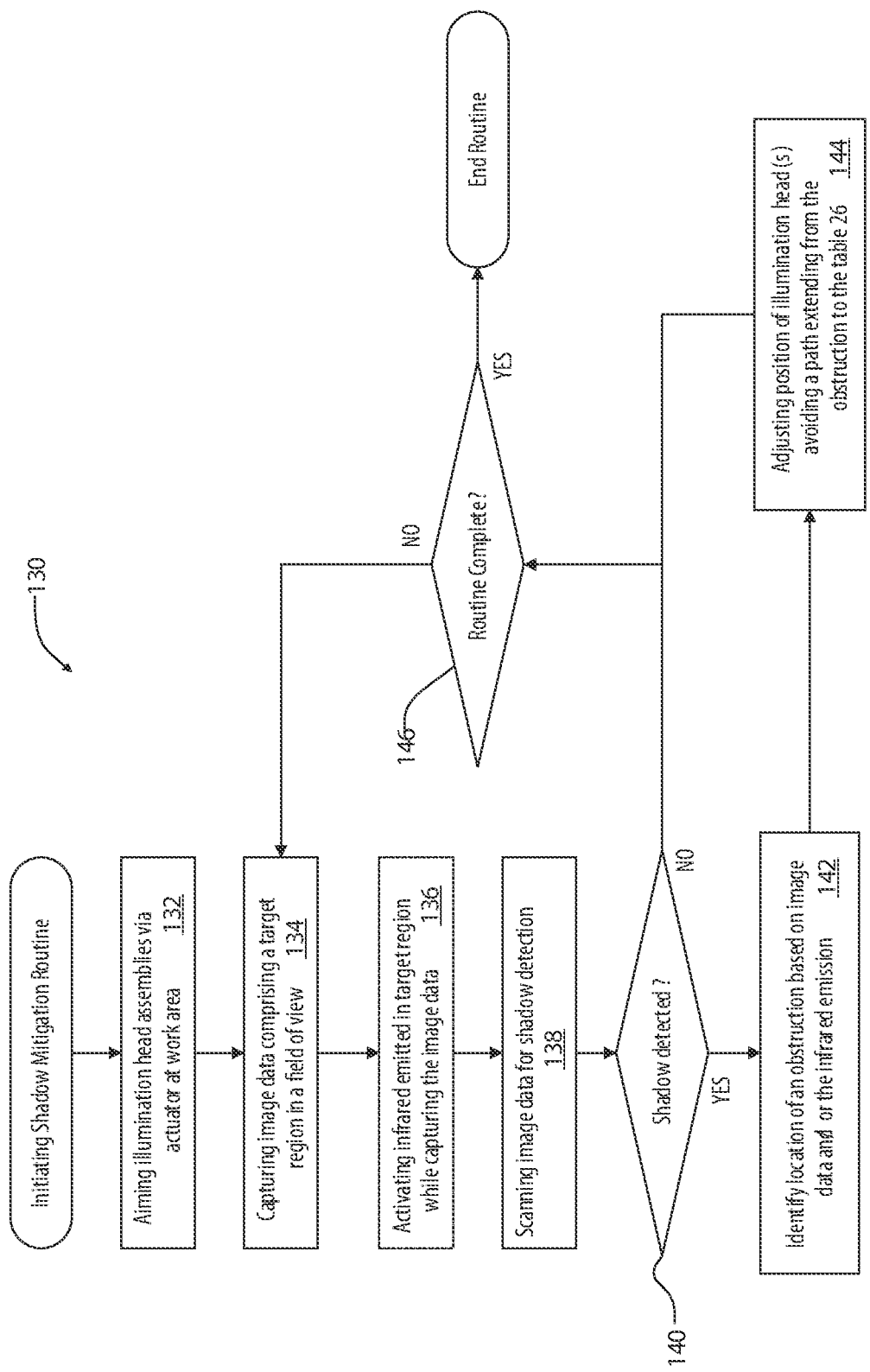
FIG. 6 is a flowchart demonstrating a shadow mitigation routine for adaptive lighting.

Referring to FIG. 6, a flowchart is shown demonstrating a shadow mitigation routine 130 for adaptive lighting. The routine 130 may begin by maneuvering a plurality of the articulating head assemblies 100 to direct the lighting modules 90 at the surgical field 30 (132). Once the lighting modules 90 are directed at the surgical field 30, the controller 40 may control the imager(s) 22 to capture image data in the field of view 50 (134). While capturing the image data, the controller 40 may additionally activate the infrared emitters 60 to project the infrared emission 62 into the surgical field 30 (136). A processor of the controller 40 may then process the image data to identify one or more shadows 38 (138). The shadows 38 may be detected based on variations in pixel intensity, which may correspond to blockages or dim regions in the surgical field 30.

In step 140, the controller 40 may determine whether a shadow 38 is detected. If one or more shadows 38 are detected, the controller 40 may continue to attempt to identify a location of the obstruction based on the image data, which may include the infrared dots 64 of the infrared emission 62 (142). Based on the image data, the controller 40 may control the positioning device 54 (e.g., the actuators 102) to adjust an aim of one or more of the lighting modules 90 to avoid a path extending between the table 26 in the surgical field 30 and the obstruction (144). In this way, the system 10 may detect and verify whether the illumination from the lighting modules 90 had effectively illuminated the shadows 38 in the operating region throughout operation. Following the adjustment of the aim in step 144 or if the shadow 38 is not detected in step 140, the controller may determine if the routine 130 is complete in step 146. If the routine is complete, the controller 40 may end the routine and position the head assemblies in their home positions. If the routine is not complete in step 146, the routine may return to step 134 and monitor the image data in the surgical field 30.

In some implementations, the obstructions may similarly be identified based on a depth image data that may be captured by the imagers 22 in a stereoscopic configuration. As previously discussed, the imagers 22 may be incorporated in one or more of the lighting modules 90 and/or various components of the system 10. Based on the depth image data, the system 10 may be configured to identify that the light emitted from one or more of the lighting modules 90 is reflected from the obstruction and reflected back in the depth image data at a depth that differs from one or more of the other lighting modules 90. Based on the difference in depth, the controller 40 of the system 10 may be configured to identify that one or more of the emissions from the light sources 20 of the lighting modules 90 is blocked by the obstructions. In response to the detection, the controller 40 may activate an additional or alternative lighting module 90 to illuminate the region of interest, which may be confirmed by illuminating the region having a greater depth in the depth image data relative to the obstruction.

Figure 7:
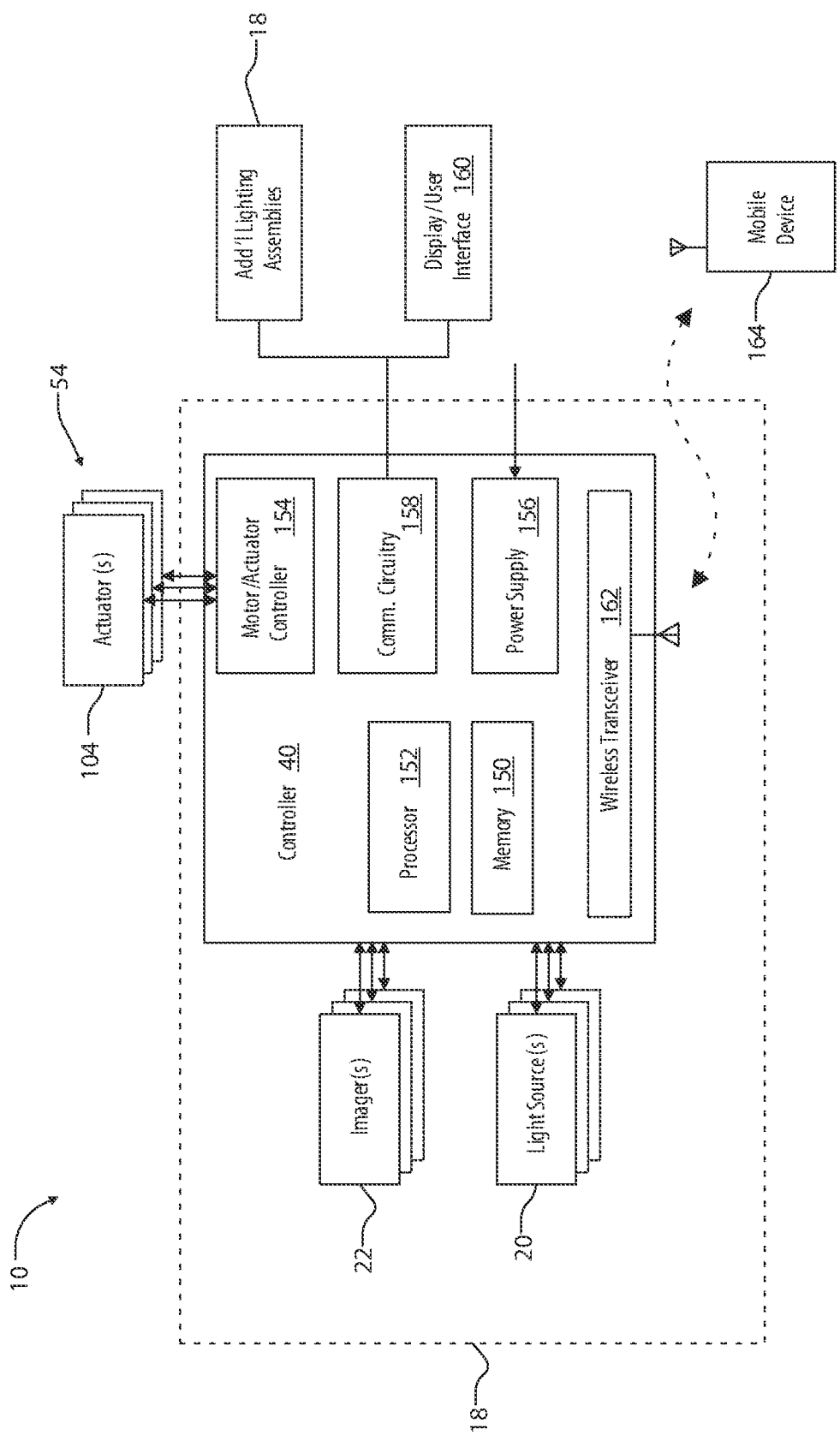
FIG. 7 is a block diagram of an illumination system in accordance with the disclosure.

Referring to FIG. 7, a block diagram of an illumination system 10 is shown. As discussed herein, the illumination system 10 may include one or more imagers 22 configured to capture image data from the surgical suite 14 and/or from the surgical field 30. The imagers 22 may be configured to relay visual information to the controller 40 of the illumination system 10. The controller may include a memory 150 and a processor 152. The memory 150 may store computer executable commands (e.g., routines) which are controlled by the processor 152. According to various examples, the memory 150 may include a light control routine and/or an image analyzing routine. In exemplary embodiments, the memory 150 may include the disinfection control routine 110 and/or the shadow mitigation routine 130.

Once the image analyzing routine has processed the image data from the imager 22, the controller 40 may communicate one or more control instructions to a motor or actuator controller 154. In response to the control signals, the motor controller 154 may control the actuators 102*a*, 102*b* or the positioning devices 54 to move, steer, or otherwise adjust an orientation of the light assemblies 18. In this way, the controller 40 may direct the lighting assemblies 18 to emit light and/or direct the field of view 50 to a desired location. The system 10 may additionally comprise one or more power supplies 156. The power supplies 156 may provide for one or more power supplies or ballasts for various components of the lighting assembly 18 as well as the actuators 102a, 102b or positioning devices 54.

In some embodiments, the system 10 may further comprise one or more communication circuits 158, which may be in communication with the processor 152. The communication circuit 158 may be configured to communicate data and control information for operating the system 10 to a display or user interface 160. The interface 160 may comprise one or more input or operational elements configured to control the system 10 and communicate data identified by the gauge system 10. The communication circuit 158 may further be in communication with additional lighting assemblies 18, which may operate in combination as an array of lighting assemblies. The communication circuit 158 may be configured to communicate via various communication protocols. For example, communication protocols may correspond to process automation protocols, industrial system protocols, vehicle protocol busses, consumer communication protocols, etc. Additional protocols may include, MODBUS, PROFIBUS, CAN bus, DATA HIGHWAY, DeviceNet, Digital multiplexing (DMX512), or various forms of communication standards.

In various embodiments, the system 10 may comprise a variety of additional circuits, peripheral devices, and/or accessories, which may be incorporated into the system 10 to provide various functions. For example, in some embodiments, the system 10 may comprise a wireless transceiver 162 configured to communicate with a mobile device 164. In such embodiments, the wireless transceiver 162 may operate similar to the communication circuit 158 and communicate data and control information for operating the system 10 to a display or user interface 160 of the mobile device 164. The wireless transceiver 162 may communicate with the mobile device 164 via one or more wireless protocols (e.g. Bluetooth®; Wi-Fi (802.11a, b, g, n, etc.); ZigBee®; and Z-Wave®; etc.). In such embodiments, the mobile device 164 may correspond to a smartphone, tablet, personal data assistant (PDA), laptop, etc.

In various embodiments, the light sources 20 may be configured to produce un-polarized and/or polarized light of one-handedness including, but not limited to, certain liquid crystal displays (LCDs), laser diodes, light-emitting diodes (LEDs), incandescent light sources, gas discharge lamps (e.g., xenon, neon, mercury), halogen light sources, and/or organic light-emitting diodes (OLEDs). In polarized light examples of the light sources 20, the light sources 20 are configured to emit a first-handedness polarization of light. According to various examples, the first-handedness polarization of light may have a circular polarization and/or an elliptical polarization. In electrodynamics, circular polarization of light is a polarization state in which, at each point, the electric field of the light wave has a constant magnitude, but its direction rotates with time at a steady rate in a plane perpendicular to the direction of the wave.

As discussed, the light assemblies 18 may include one or more of the light sources 20. In examples including a plurality of light sources 20, the light sources 20 may be arranged in an array. For example, an array of the light sources 20 may include an array of from about 1×2 to about 100×100 and all variations therebetween. As such, the light assemblies 18 including an array of the light sources 20 may be known as pixelated light assemblies 18. The light sources 20 of any of the light assemblies 18 may be fixed or individually articulated. The light sources 20 may all be articulated, a portion may be articulated, or none may be articulated. The light sources 20 may be articulated electromechanically (e.g., a motor) and/or manually (e.g., by a user). In static, or fixed, examples of the light sources 20, the light sources 20 may be assigned to focus on various predefined points (e.g., on a patient and/or on the table 26).

Modifications of the disclosure will occur to those skilled in the art and to those who make or use the disclosure. Therefore, it is understood that the embodiments shown in the drawings and described above are merely for illustrative purposes and not intended to limit the scope of the disclosure, which is defined by the following claims as interpreted according to the principles of patent law, including the Doctrine of Equivalents.

It will be understood by one having ordinary skill in the art that construction of the described disclosure, and other components, is not limited to any specific material. Other exemplary embodiments of the disclosure disclosed herein may be formed from a wide variety of materials unless described otherwise herein.

For purposes of this disclosure, the term "coupled" (in all of its forms: couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

It is also important to note that the construction and arrangement of the elements of the disclosure, as shown in the exemplary embodiments, is illustrative only. Although only a few embodiments of the present innovations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts, or elements shown as multiple parts may be integrally formed, the operation of the interfaces may be reversed or otherwise varied, the length or width of the structures and/or members or connector or other elements of the system may be varied, and the nature or numeral of adjustment positions provided between the elements may be varied. It should be noted that the elements and/or assemblies of the system may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

It will be understood that any described processes, or steps within described processes, may be combined with other disclosed processes or steps to form structures within the scope of the present disclosure. The exemplary structures and processes disclosed herein are for illustrative purposes and are not to be construed as limiting.

It is also to be understood that variations and modifications can be made on the aforementioned structures and methods without departing from the concepts of the present disclosure, and further, it is to be understood that such concepts are intended to be covered by the following claims, unless these claims, by their language, expressly state otherwise. Further, the claims, as set forth below, are incorporated into and constitute part of this Detailed Description.

As used herein, the term "about" means that amounts, sizes, formulations, parameters, and other quantities and characteristics are not and need not be exact, but may be approximate and/or larger or smaller, as desired, reflecting tolerances, conversion factors, rounding off, measurement error, and the like, and other factors known to those of skill in the art. When the term "about" is used in describing a value or an end-point of a range, the disclosure should be understood to include the specific value or end-point referred to. Whether or not a numerical value or end-point of a range in the specification recites "about," the numerical value or end-point of a range is intended to include two embodiments: one modified by "about," and one not modified by "about." It will be further understood that the end-points of each of the ranges are significant both in relation to the other end-point and independently of the other end-point.

The terms "substantial," "substantially," and variations thereof as used herein are intended to note that a described feature is equal or approximately equal to a value or description. For example, a "substantially planar" surface is intended to denote a surface that is planar or approximately planar. Moreover, "substantially" is intended to denote that two values are equal or approximately equal. In some embodiments, "substantially" may denote values within about 10% of each other, such as within about 5% of each other, or within about 2% of each other.

What is claimed is:

1. An illumination system, comprising:
   a first light assembly comprising at least one first light source positioned within the light assembly and emitting light;
   at least one imager configured to capture image data;
   a controller configured to:
      process data from the at least one imager; and
      control the operation of the first light assembly; and
   a wearable device comprising at least one second light source
   wherein the wearable device causes the controller to direct light from the at least one light assembly to a location being viewed by a user.

2. The illumination system of claim 1, wherein the at least one imager is coupled to the first light assembly.

3. The illumination system of claim 1, wherein the at least one imager is disposed within the wearable device.

4. The illumination system of claim 1, wherein the controller is configured to identify shadows within the captured image data.

5. The illumination system of claim 4, wherein the controller is configured to control the first light assembly to alter one of the intensity, focus, and origin of the light emitted from the light assembly to illuminate the shadows.

6. The illumination system of claim 1, further comprising a second light assembly; and
   wherein the second light assembly is in communication with the controller.

7. The illumination system of claim 6, wherein the first light assembly and the second light assembly are both supported by a track system.

8. The illumination system of claim 7, wherein the first light assembly and the second light assembly are configured to be mechanically connectable to one another.

9. The illumination system of claim 7, wherein the first light assembly and the second light assembly are moveable relative to one another.

10. The illumination system of claim 6, wherein the second light assembly receives electrical power through the first light assembly.

11. The illumination system of claim 1, further comprising a mirror having a reflective surface;
    wherein the reflective surface of the mirror is a concave surface; and
    wherein the at least one first light source is configured to emit light toward the reflective surface of the mirror.

12. The illumination system of claim 11, wherein the at least one first light source is disposed in proximity to a surgical table; and
    wherein the mirror is disposed so as to reflect the light toward the surgical table.

13. The illumination system of claim 1, wherein one of the at least one first light sources is capable of producing light having one of a circular and an elliptical polarization.

14. The illumination system of claim 13, further comprising an optical filter incorporated into the wearable device and configured to allow a first-handed polarization of light to pass through and to eliminate a second-handed polarization of light.

15. The illumination system of claim 1, wherein the wearable device comprises one of headwear and a garment.

16. The illumination system of claim 1, wherein one of the at least one of the first light sources is configured to emit light that excites a fluorescent dye.

17. The illumination system of claim 16, wherein the wearable device comprises eyewear having a portion that a user can look through; and
    wherein the wearable device is configured to allow light having the wavelength emitted from the fluorescent dye to pass through the portion of the wearable device that the user can look through.

18. A wearable device, comprising:
    at least one light source; and
    at least one guidance system;
    wherein the wearable device is in communication with at least one imager configured to capture image data from one of a surgical field and a surgical suite;
    wherein the guidance system includes a laser configured to emit one of visible and non-visible light;
    wherein the light emitted from the guidance system is tracked by the imager and communicated to an illumination system, and
    wherein the illumination system, in response to receiving communication from the guidance system, emits light from a light assembly directed to where a user is looking.

19. The wearable device of claim 18, wherein the at least one guidance system is configured to indicate where the user is looking.

* * * * *